United States Patent
Thampi et al.

(10) Patent No.: US 6,982,354 B2
(45) Date of Patent: Jan. 3, 2006

(54) PREPARATION OF KETONE CONTAINING CYCLIC COMPOUNDS

(75) Inventors: Jegadeesh Thampi, Karnataka (IN); Umesh Krishna Hasyagar, Karnataka (IN); Anju S. Shukla, Maharashtra (IN); Pramod Kumbhar, Karnataka (IN)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 10/770,001

(22) Filed: Feb. 2, 2004

(65) Prior Publication Data

US 2005/0171386 A1    Aug. 4, 2005

(51) Int. Cl.
*C07C 45/38* (2006.01)
(52) U.S. Cl. .................. 568/361; 568/365; 568/373; 568/374
(58) Field of Classification Search ............... 568/361, 568/365, 373, 374
See application file for complete search history.

(56) References Cited

U.S. PATENT DOCUMENTS

| 2,849,489 | A | 8/1958 | Buchner et al. | ............ 260/586 |
| 4,133,965 | A | 1/1979 | Kato et al. | .................. 568/723 |
| 4,709,061 | A | 11/1987 | Brunke et al. | ............. 549/544 |
| 5,266,729 | A | 11/1993 | Bach et al. | ................. 568/361 |

*Primary Examiner*—Samuel Barts
*Assistant Examiner*—Sikarl A. Witherspoon

(57) ABSTRACT

A method of preparing a polycyclic compound containing a ketone functionality comprising:
  reacting a mixture comprising a catalyst, a reactant compound and an amount of water greater than or equal to 3 weight percent (wt %) based on the weight of the reactant compound; wherein said catalyst comprises nickel and base and said reactant compound comprises at least two fused rings, A and B wherein ring A is a saturated ring or ring system having 5 to 7 cyclic carbons and substituted with a hydroxyl functionality and ring B is a non-aromatic unsaturated ring having 5 to 6 cyclic carbons; and
  converting the hydroxyl functionality of ring A to a ketone functionality and non-aromatic unsaturated ring B to a saturated ring.

25 Claims, No Drawings

PREPARATION OF KETONE CONTAINING CYCLIC COMPOUNDS

BACKGROUND

The disclosure generally relates to methods for the preparation of compounds comprising a ketone functionality, particularly from compounds comprising a hydroxyl functionality.

One approach to the preparation of fully saturated polycyclic compounds comprising a ketone functionality from unsaturated polycyclic compounds comprising a hydroxyl functionality has employed Raney nickel catalyst. Methods employing the Raney nickel catalyst are attractive because the Raney nickel catalyst is less expensive than many other nickel based catalysts, as well as readily available and recyclable. Unfortunately, attempts employing a Raney nickel catalyst have resulted in low selectivity and conversions. Use of Raney nickel catalyst in the presence of water or alkali has been discouraged since the presence of water in the reaction is said to provide poorer yields and the presence of alkali is said to have disturbing effects on the rearrangement. Nickel/magnesia catalysts having specific molar ratio of nickel to magnesia (0.0075–0.075:1) are disclosed in the art. The reaction using these nickel/magnesia catalyst occurs with good selectivity and good conversion although the reaction times are long.

Fully saturated polycyclic compounds comprising a ketone functionality are suitable for use as a component for the preparation of perfumes. Bisphenols prepared using these ketone containing compounds find utility in the preparation of polycarbonates and polyesters.

There is a need for a process which ensures a commercially viable, substantially reproducible process with the avoidance of undesirable byproducts for the preparation of fully saturated polycyclic compounds comprising a ketone functionality in high yield and purity.

BRIEF DESCRIPTION

A method of preparing a polycyclic compound containing a ketone functionality comprising:
reacting a mixture comprising a catalyst, a reactant compound and an amount of water greater than or equal to 3 weight percent (wt %) based on the weight of the reactant compound; wherein said catalyst comprises nickel and base and said reactant compound comprises at least two fused rings, A and B wherein ring A is a saturated ring or ring system having 5–7 cyclic carbons and substituted with a hydroxyl functionality and ring B is a non-aromatic unsaturated ring having 5 to 6 cyclic carbons; and
converting the hydroxyl functionality of ring A to a ketone functionality and the non-aromatic unsaturated ring B to a saturated ring.

The above-described method may be understood more readily by reference to the following detailed description of the various features of the disclosure and the examples included therein.

DETAILED DESCRIPTION

Disclosed herein are facile methods for preparation of the compounds having fused cyclic ring systems containing a ketone functionality in high yields and selectivities with a shorter reaction time than earlier known methods. The method of preparing a polycyclic compound containing a ketone functionality comprises:
reacting a mixture of a catalyst comprising nickel and base, a reactant compound and an amount of water greater than or equal to 3 weight percent based on the weight of the reactant compound wherein said reactant compound comprises at least two fused rings, A and B wherein ring A is a saturated ring or ring system having 5–7 cyclic carbons and substituted with a hydroxyl functionality and ring B is a non-aromatic unsaturated ring having 5–7 cyclic carbons; and converting the hydroxyl functionality of ring A to a ketone functionality and the non-aromatic unsaturated ring B to a saturated ring. Ring A may be a bicyclo system.

Ring A and Ring B may be directly fused in that they share one or more common carbon—carbon bonds. Alternately Ring A and Ring B may be indirectly fused with a ring system containing 5 to 6 cyclic carbons and both Ring A and Ring B independently have one or more carbon—carbon bonds in common with the ring system.

In one embodiment the reactant compound comprises two fused rings, A and B wherein ring A is a saturated ring having 5 cyclic carbons and substituted with a hydroxyl functionality and ring B is a non-aromatic unsaturated ring having 5 cyclic carbons. In this embodiment, the fused rings A and B may together form a bicyclo ring.

Ring A, Ring B and any other rings present may independently be substituted with one or more alkyl substituents having up to 4 carbons provided that the location of the substitution does not prevent the reaction.

The singular forms "a", "an" and "the" include plural referents unless the context clearly dictates otherwise. "Optional" or "optionally" means that the subsequently described event or circumstance may or may not occur, and that the description includes instances where the event occurs and instances where it does not.

Unless otherwise specified, the term "alkyl" as used herein is intended to designate straight chain alkyls and branched alkyls. The straight chain and branched alkyl groups include as illustrative non-limiting examples, methyl, ethyl, n-propyl, isopropyl, n-butyl, iso-butyl and tertiary-butyl groups.

Exemplary reactant compounds include compounds of the formula:

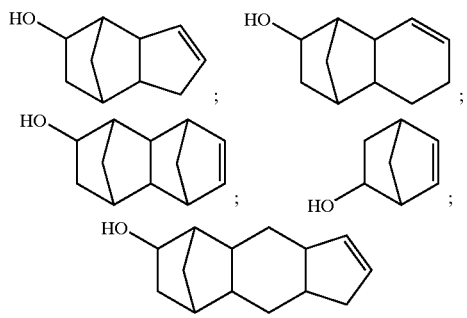

and combinations of two or more of the foregoing compounds.

Exemplary cyclic compounds containing a ketone functionality include

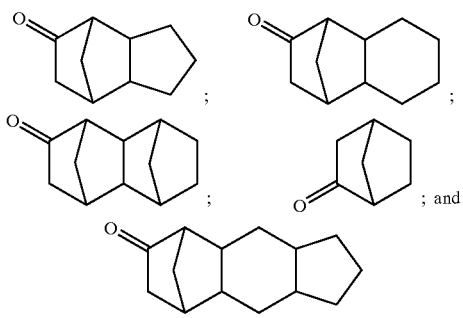

In one embodiment is provided the reaction of a polycyclic alcohol (known as tricyclo[5.2.1.0$^{2,6}$]decenol or cydecanol) having the formula

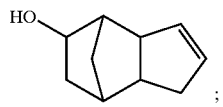

with water and a catalyst comprising nickel and base produces a polycyclic compound containing a ketone functionality (known as tricyclo[5.2.1.0$^{2,6}$]decanone or TCD ketone) of the formula;

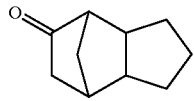

The conversions of the cyclic unsaturated compound containing hydroxyl functionality and the selectivity towards formation of a cyclic saturated compound containing a ketone functionality appears to increase when the reaction is carried out in the presence of water by employing a catalyst comprising nickel and base.

The base can be already present in the catalyst composition or added separately. The base may comprise an inorganic base, an organic base or a mixture of the foregoing bases in sufficient quantity to obtain the desired pH. The inorganic base may be selected from the group consisting of sodium hydroxide, magnesium hydroxide, magnesium oxide, sodium carbonate, potassium hydroxide, calcium hydroxide, sodium silicate, potassium carbonate, sodium bicarbonate, potassium bicarbonate, ammonia, ammonium hydroxide and a mixture of two or more of the foregoing bases. The organic base may be an alkyl amine, aryl amine or a mixture of two or more of the foregoing bases. The organic base may be selected from the group consisting of aniline, pyridine, piperidine, methyl amine, propyl amine, butyl amine and a mixture of two or more of the foregoing bases. In one embodiment the base is sodium hydroxide.

The amount of water in the reaction may also impact the selectivity of the reaction. In one embodiment the reaction contains about 3 to about 10 weight percent water, based on the weight of reactant compound. Within this range, the amount of water may be greater than or equal to about 4 weight percent. Also within this range, the amount of water may be less than or equal to about 7 weight percent. The source of water in the reaction system is dependent on the water present in the reactant compound and the water added, if any, with the catalyst. In some instances the reactant compound contains about 3 to about 5 wt % water in addition to other impurities. The water content in the catalyst varies from zero to about 50 wt % depending on the catalyst employed.

As mentioned above, in case of commercially available catalyst compositions like Raney nickel where the finely divided nickel is available as a slurry in water at a basic pH, the catalyst can be directly employed. The ratio of nickel to water in commercially available Raney nickel is generally about 50:50 weight ratio and the pH is basic. If required the pH of the Raney nickel is adjusted to a pH value greater than or equal to about 8.

In another embodiment a catalyst composition is prepared which comprises adding a base and optionally water to the catalyst. The quantity of water added is about 3 to about 7 weight percent based on the weight of the reactant compound. The amount of base present is sufficient to obtain a catalyst composition with a pH greater than equal or equal to about 8. Given that the majority of the described reactant compounds are pH neutral, the pH of the reaction is substantially the same as the pH of the catalyst.

Specific examples of the catalyst include but are not limited to Raney nickel, supported nickel catalysts, Ponder nickel catalysts, and nickel alloys. The support material that is suitable for use in supported-nickel catalysts may be selected from the group including silicates, such as calcium silicate, magnesium silicate, aluminum silicate, alumina, silica, kieselguhr and mixtures of the foregoing support materials. The supported nickel catalyst may be selected from the group consisting of, but not limited to, nickel on silica and nickel/magnesium oxide supported on silica. Nickel alloy may be selected from the group consisting of, but not limited to, aluminum-nickel alloy, nickel-vanadium alloy, magnesium-nickel alloy and copper-nickel alloy.

Again as mentioned above, some catalysts may already comprise a base and it may not be necessary to add any additional base. In the case of nickel/magnesium oxide catalyst the nickel already exists with a base (magnesium oxide) and is supported on an inert media like silica. The ratio of nickel to magnesium oxide employed is about 0.1:1 to about 0.5:1, more particularly the ratio of nickel to magnesium oxide employed is about 0.18:1 to about 0.33:1 in the nickel/magnesium oxide supported on silica catalyst. The water necessary for the reaction may be provided by the reactant compound or added separately.

The amount of the catalyst comprising nickel added either as a composition containing nickel, base and water or when the base is included with the nickel on the support system is about 1 to 5 weight percent based on weight of the reactant compound.

Hydrogen gas or hydrogen-containing gas mixture may optionally be employed in the conversion of the polycyclic unsaturated compound containing a hydroxyl functionality to a polycyclic saturated compound containing a ketone functionality. The hydrogen containing gas can be introduced at the beginning of the reaction or after the reaction has begun. The hydrogen containing gas mixture may comprise nitrogen, ambient air, helium argon or a combination of two or more of the foregoing. The amount of hydrogen or hydrogen-containing gas used is enough to maintain a pressure of about 5 to about 40 Newtons per square centimeter over and above the autogenous pressure generated in the system when the system is heated to the reaction temperature of about 170° C. to about 300° C.

The reaction mixture may optionally comprise a solvent miscible with the alcohol compound. Exemplary solvents include alcohols containing 1 to about 4 carbon atoms and sulfolane. Preferred alcohols include methyl alcohol, ethyl alcohol, isopropyl alcohol and a mixture of two or more of the foregoing alcohols.

The temperature at which the alcohol compound is converted to the keto compound is about 170° C. to about 300° C. Within this range the temperature may be greater than or equal to about 200° C., preferably greater than or equal to about 230° C. Also within this range the temperature may be less than or equal to about 270° C., preferably less than or equal to about 250° C.

The process described hereinabove can be conducted either in a batch process, or in a semi-continuous process or continuous process. When performed in batch mode the reaction of the compound containing hydroxyl functionality and catalyst is carried out for about 1.5 hours to about 5 hours. Generally, the reaction is carried out for about 2 hours to about 4 hours to achieve a satisfactory conversion of compound containing hydroxyl functionality to the corresponding ketone containing compound. In the continuous mode, the weighted hourly space velocity varies from about 0.5 to about 2.0. In a one embodiment, a weighted hourly space velocity of about 0.75 to about 1.0 may be used to achieve a satisfactory conversion of the alcohol compound to the corresponding ketone containing compound.

The ketones described herein may be used in the preparation of polycyclic bisphenols. Bisphenols may be prepared by suitable techniques such as by the condensation of the polycyclic ketone with a phenolic compound in the presence of a homogenous or heterogenous acid catalyst. The homogenous acid catalyst may be selected from hydrochloric acid, sulfuric acid, toluene sulfonic acid or methionic acid and a promoter like 3-mercaptopropionic acid or methyl mercaptan as a catalyst and an ion exchange resin catalyst may be used as the heterogenous catalyst The resulting bisphenols may be used for the preparation of polycarbonates and polyesters, which are valuable in the production of films, filaments, and shaped articles having excellent high-temperature properties and solubility in low boiling solvents. The resulting bisphenols may be used in of polycarbonates. Linear polycarbonates can be prepared by condensation of phosgene or bischloroformate of a diol or a mixture of these with the polycyclic bisphenols. Polycarbonates from polycyclic bisphenols may be prepared by adding phosgene and/or a bischloroformate of a diol, in an aqueous alkaline medium and methylene chloride system or in the presence of tertiary amine and methylene chloride. The polycarbonates may also be prepared by the ester interchange process by heating the bisphenol with a diaryl carbonate and a suitable catalyst like oxides, hydrides, hydroxides of alkali and alkaline earth metals and the free alkali or alkaline earth metals under reduced pressure. Linear dicarboxylic acid polyesters can be prepared by condensation of one or more organic dicarboxylic acids, or dicarboxylic acid diesters, with the polycyclic bisphenols. The dicarboxylic polyesters may be prepared by condensing the polycyclic bisphenols with dicarboxylic acids by ester interchange reactions between the bisphenols and esters of aliphatic, cyclo-aliphatic and aromatic dicarboxylic acids.

A further understanding of the techniques described above can be obtained by reference to certain specific examples that are provided herein for purposes of illustration only, and are not intended to be limiting.

EXAMPLES

Example 1

A mixture of tricyclo[$5.2.1.0^{2,6}$] decenol (cydecanol) (100 grams; 93 wt % cydecanol, 4 wt % water), Raney nickel (3 grams), water (2 grams) and sodium hydroxide (quantity sufficient to obtain pH of 10) was charged to a 600 milliliters pressure vessel. The reaction mixture was heated to a temperature of about 235° C. in the course of 1 hour and was maintained at said temperature for about 4 hours till a cydecanol conversion in excess of 99% was indicated when analyzed by gas chromatography (GC). The autogenous pressure built up to about 56 Newtons per square centimeter during the course of the reaction. The conversion, relative to cydecanol was 99.5% and the selectivity of the conversion to tricyclo[$5.2.1.0^{2,6}$] decanone (TCD ketone) was 94% when estimated by GC methods. Note: conversion is the percentage of cydecanol that has reacted and selectivity is the percentage of the reacted cydecanol that has led to the formation of TCD-ketone.

Example 2

A mixture of crude cydecanol (306.45 grams, cydecanol content 88 wt %, water 4 wt %), Raney nickel (11.8 grams; approx. 80 wt % Ni and 20 wt % alkaline water pH=11) was charged into a 600 milliliters pressure vessel. The reactor was purged with nitrogen gas at 35 Newtons per square centimeter after which about 7 Newtons per square centimeter pressure of nitrogen was maintained. The reaction mixture was then heated to a temperature of about 250° C., at this temperature the autogenous pressure was 114 Newtons per square centimeter. Hydrogen gas was fed into the vessel till the pressure reached about 142.1 Newtons per square centimeter. This pressure was maintained by feeding fresh hydrogen when a dip in pressure was observed. After about 3 hours 45 minutes, the conversion of cydecanol was 99.95% with a selectivity of conversion towards tricyclo [$5.2.1.0^{2,6}$] decanone of 97.79% as analyzed by GC.

Example 3

A mixture of crude cydecanol (298.95 gram, cydecanol content 88 wt %, water 4 wt %), Raney nickel (12.21 gram; approx. 80 wt % Ni and 20 wt % water, pH=11) was charged into a 600 milliliters pressure vessel. The reactor was purged thrice with nitrogen gas at 35 Newtons per square centimeter after which about 7 Newtons per square centimeter pressure of nitrogen was maintained. The reaction mixture was then heated to a temperature of about 250° C., at this temperature the autogenous pressure was 114 Newtons per square centimeter. After about 2 hours conversion, relative to cydecanol, was 99.25%, and the selectivity of conversion to TCD Ketone was 90.3% as indicated by GC analysis. Hydrogen gas was fed into the vessel till the pressure reached about 143.5 Newtons per square centimeter. This pressure was maintained by feeding fresh hydrogen when a dip in pressure was observed. After about 4 hours, the conversion of cydecanol was 99.84% with a selectivity of conversion towards tricyclo[$5.2.1.0^{2,6}$] decanone of 95.6% as indicated by GC analysis.

Example 4

A mixture of cydecanol (100 grams, 93 wt % cydecanol, 4 wt % water), and 5 grams Engelhard Ni-5249 P (Nysosel Nickel Catalyst supplied by Engelhard corp., US, Composition: nickel; 64 wt %, silica, amorphous; 16 wt % and magnesium oxide; 8 wt %) were charged into a 600 milliliters pressure vessel. The reaction mixture was then heated to a temperature of about 235° C. in the course of 1 hour and was maintained at said temperature for about 4 hours till a cydecanol conversion in excess of 99% was indicated when analyzed by gas chromatography (GC). The system pressure built up to about 52.5 N/cm$^2$ during the course of the reaction. The conversion, relative to cydecanol was 99.4% and the selectivity of conversion to TCD ketone was 95.4% when estimated by GC methods.

Comparative Example 1

A mixture of cydecanol (100 grams), Raney nickel (3 grams), water (2 grams; pH=7) was charged into a 600 milliliters pressure vessel. The catalyst was washed several times with de-ionized de-mineralized water to remove all traces of impurities or alkali present in the catalyst till the pH of the water became 7. The reaction mixture was then heated to a temperature of about 235° C. in the course of 1 hour and was maintained at said temperature for about 10 hours. The system pressure built up to about 24.5 Newtons per square centimeter (N/cm$^2$) during the course of the reaction. The conversion, relative to cydecanol was 96% and the selectivity of conversion to TCD Ketone was 73% when estimated by GC methods.

Comparative Example 2

Raney nickel (5 gram comprising 3 grams nickel and 2 grams water at pH 10) was washed repeatedly with methanol till the Raney nickel was free from water and alkali. It was again washed with cydecanol to remove methanol. This treated Raney nickel was used as the catalyst. Cydecanol was added to the treated catalyst to make the total cydecanol quantity 100 grams. The mixture of the treated catalyst and cydecanol was heated to a temperature of about 230° C. in Parr pressure vessel when the autogenous pressure developed was 70 N/cm$^2$. After about 4 hours the conversion of cydecanol was 98.3% with a selectivity towards tricyclo [5.2.1.0$^{2,6}$] decanone of 79.8%.

Table I below summarizes the results of Examples 1–4 and Comparative Examples 1–2.

TABLE I

| Example | Reaction components in addition to cydecanol | Time in hours | Cydecanol conversion in % | Tricyclo [5.2.1.0$^{2,6}$] decanone selectivity in % |
|---|---|---|---|---|
| Example 1 | Raney Ni, water and NaOH | 4.00 | 99.50 | 94.0 |
| Example 2 | Raney Ni, water, NaOH and Hydrogen | 3.75 | 99.95 | 97.8 |
| Example 3 | Raney Ni, water, NaOH and Hydrogen addition in between | 4.00 | 99.84 | 95.5 |
| Example 4 | Engelhard Ni-5249 P | 12.0 | 99.40 | 95.4 |
| Comparative Example 1 | Raney Nickel and water | 10.0 | 96.00 | 73.0 |
| Comparative Example 2 | Raney Ni alone | 4.00 | 98.30 | 79.8 |

Example 6

Cydecanol (purity 93 wt %, 4t % water) was reacted with Engelhard Ni 5256E (Nickel, 31 wt %, Nickel Oxide, 32 wt %, Silica Amorphous, 24 wt % and Magnesium Oxide, 13 wt %) catalyst in a continuous mode at a weighted hour space velocity (WHSV) of 0.95. The weight of the catalyst loaded in the reactor was 5.28 grams. The catalyst bed was activated by loading the reactor with catalyst and glass beads and heating the reactor to 250° C. Hydrogen was passed trough the bed at a flow rate of 0.1 ml/min for 16 hrs and the temperature was maintained at 250° C. The reactor pressure was maintained at 50 N/cm$^2$. After this hydrogen was released and the catalyst bed temperature was reduced to 230° C. and nitrogen was passed through the bed at a flow rate of 0.1 ml/min and the reactor pressure was maintained at 50 N/cm$^2$. Nitrogen flushing was done for 1 hr and then nitrogen was released. The activated catalyst bed was then maintained at a temperature of about 230° C. Cydecanol was pumped through the catalyst bed at a flow rate of 5 grams per hour. The reactor pressure was set for 15 N/cm$^2$. The autogenous pressure of reaction was 10 N/cm$^2$. The cydecanol conversion and TCD ketone selectivities were monitored by GC. It took 6 hrs for the reactor to stabilize. The bed temperature was raised to about 250° C. to maintain the catalyst activity. Table II gives the conversion of cydecanol and TCD ketone selectivity with respect to time and temperature.

TABLE II

| Time in Hours | Temperature ° C. | Cydecanol Conversion % | tricyclo [5.2.1.0$^{2,6}$] decanone Selectivity, % |
|---|---|---|---|
| 0 | 230 | 0.00 | 0.00 |
| 6 | 230 | 88.11 | 89.47 |
| 22 | 230 | 99.53 | 95.42 |
| 25 | 230 | 99.83 | 96.07 |
| 28 | 230 | 100.00 | 96.55 |
| 30 | 230 | 100.00 | 96.34 |
| 94 | 230 | 98.84 | 96.77 |
| 99.5 | 235 | 97.63 | 91.80 |
| 102.5 | 235 | 99.37 | 93.24 |
| 118.5 | 235 | 99.70 | 93.70 |
| 120 | 235 | 99.62 | 92.68 |
| 125 | 240 | 99.66 | 92.97 |
| 142.5 | 240 | 99.63 | 92.13 |
| 148.5 | 245 | 99.63 | 92.67 |
| 165.5 | 245 | 99.53 | 88.19 |
| 168.5 | 250 | 99.27 | 88.53 |
| 173 | 250 | 99.31 | 88.39 |
| 190 | 250 | 99.71 | 92.60 |
| 196 | 250 | 99.69 | 92.84 |

Example 7

A mixture of cydecanol 100 grams (93% cydecanol, 4% water), Raney nickel catalyst 5 grams (3 grams nickel and water 2 grams at pH 11) were charged into a 600 milliliters pressure vessel and heated to 230° C. The autogenous temperature that developed in the system was about 18.9 N/cm$^2$. The reaction was maintained at this temperature and pressure for about 2 hours and then pressurized with 24.5 N/cm$^2$ hydrogen and then maintained for another 2 hours. The conversion of cydecanol and selectivity towards tricyclo [5.2.1.0$^{2,6}$] decanone were determined by GC. The catalyst was recovered and used for additional 4 cycles, the results of which are tabulated below in Table III.

TABLE III

| Cycle number | Catalyst (grams) | Cydecanol (grams) | Conversion of cydecanol % | Selectivity to tricyclo[5.2.1.0$^{2,6}$] decanone % |
|---|---|---|---|---|
| 1 | 5 | 100 | 99.4 | 95.4 |
| Recycle 1 | 4 | 80 | 99.4 | 94 |
| Recycle 2 | 4 | 80 | 99.5 | 90.84 |
| Recycle 3 | 4 | 80 | 99.3 | 83.3 |
| Recycle 4 | 4 | 80 | 99.3 | 83.6 |
| Recycle 5 | 4* | 80 | 99.5 | 93.2 |

*in the last recycle 0.5 gram water of pH 11 was added.

Gas Chromatographic (GC) method was used to quantify the conversion of cyclic unsaturated compound having hydroxy functionality to cyclic saturated compound having ketone functionality. A Supelcowax-10 column, length: 30 meter, inner diameter 0.32 millimeters and thickness 1.0 micrometers was used for the analysis. The maximum oven temperature was maintained at 220° C. and the Injection temperature and detector temperature was 230° C. The column was eluted with helium at a flow rate of 24 milliliters per minute (ml/min) and with hydrogen at a flow rate of 45 ml/min. Hydrogen and helium were simultaneously pumped into the column. The flow rate of sample in the column was maintained at 1.00 ml/min and amount of sample injected was 1.0 micro liter. The total run time was 37 min. The selectivity and conversions are directly measured on the basis of percentage area under the curve from the gas chromatogram.

Unexpectedly it has been observed that employing catalyst comprising nickel and a base in the presence of water provides very high conversions of the cyclic unsaturated compounds containing hydroxyl functionality and very high selectivity towards the formation of cyclic saturated compounds containing ketone functionality. Further relatively high conversions and selectivities are obtained when the same catalyst is recycled.

While only certain features of the disclosure have been illustrated and described herein, many modifications and changes will occur to those skilled in the art. Therefore, it is to be understood that the appended claims are intended to cover all such modifications and changes within the true spirit of the disclosure.

We claim:

1. A method of preparing a polycyclic compound containing a ketone functionality comprising:
   reacting a mixture comprising a catalyst, a reactant compound and an amount of water greater than or equal to 3 weight percent based on the weight of the reactant compound; wherein said catalyst comprises nickel and base and said reactant compound comprises at least two fused rings, A and B wherein ring A is a saturated ring or ring system having 5 to 7 cyclic carbons and substituted with a hydroxyl functionality and ring B is a non-aromatic unsaturated ring having 5 to 6 cyclic carbons; and
   converting the hydroxyl functionality of ring A to a ketone functionality and the non-aromatic unsaturated ring B to a saturated ring.

2. The method of claim 1, wherein Ring A is a bicyclo ring system containing 7 cyclic carbons.

3. The method of claim 1, wherein Ring A and Ring B together from a bicyclo ring system.

4. The method of claim 1, wherein the method further comprises addition of hydrogen gas or hydrogen-containing gaseous mixture.

5. A method of claim 4, wherein said hydrogen-containing gaseous mixture comprises nitrogen, ambient air, helium, argon or a combination of two or more of the foregoing.

6. The method of claim 1 wherein the mixture further comprises a solvent miscible with the reactant compound.

7. The method of claim 1 wherein ring A is substituted with one or more alkyl substituents having up to 4 carbons.

8. The method of claim 1 wherein ring B is substituted with one or more alkyl substituents having up to 4 carbons.

9. The method of claim 1, wherein the reactant compound is selected from the group consisting of compounds of the formula:

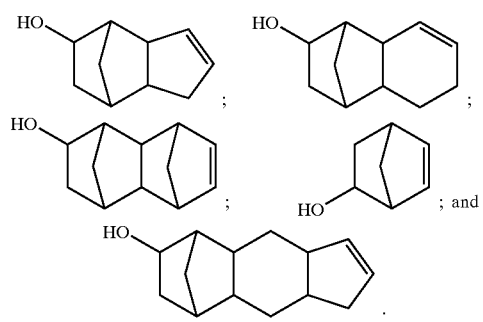

10. A method of claim 1, wherein the polycyclic cyclic compound containing a ketone functionality is selected from the group consisting of:

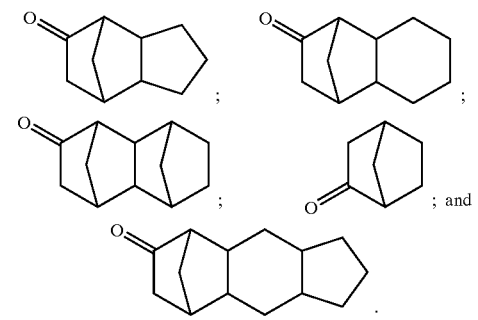

11. The method of claim 1, wherein said catalyst comprising nickel is selected from the group consisting of Raney nickel, supported nickel catalysts, Ponder nickel catalysts, and nickel alloys.

12. The method of claim 11, wherein said supported nickel catalyst is selected from the group consisting of nickel on silica and nickel/magnesium oxide supported on silica.

13. The method of claim 11, wherein said nickel alloy is selected from the group consisting of aluminum-nickel alloy, nickel-vanadium alloy, magnesium-nickel alloy and copper-nickel alloy.

14. The method of claim 1, wherein said catalyst comprising nickel is Raney nickel.

15. The method of claim 14, wherein said catalyst is recycled.

16. The method of claim 1, wherein said catalyst comprising nickel is nickel/magnesium oxide supported on silica wherein, the ratio of nickel to magnesium oxide is about 0.1:1 to about 0.5:1.

17. The method of claim 1, wherein the amount of water is about 3% to about 10% based on the weight of said reactant compound on dry basis.

18. The method of claim 1, wherein the reaction occurs at a temperature of about 170° C. to about 300° C.

19. The method of claim 1, wherein said method is carried out in a batch mode.

20. The method of claim 19, wherein said batch mode is carried out for about 1.5 to about 4 hours.

21. The method of claim 1, wherein said method is carried out in a continuous mode.

22. The method of claim 21, wherein said continuous mode is carried out at a weighted hourly space velocity of about 0.5 to about 2.0.

23. The method of claim 1, wherein the catalyst is recycled.

24. A method of preparing a polycyclic compound containing a ketone functionality comprising:

reacting a mixture comprising a catalyst, a reactant compound and an amount of water greater than or equal to 3 weight percent based on the weight of the reactant compound; wherein said catalyst comprises water and base and said reactant compound comprises two fused rings, A and B wherein ring A is a saturated ring system having 5 cyclic carbons and substituted with a hydroxyl functionality and ring B is a non-aromatic unsaturated ring having 5 cyclic carbons; and converting the hydroxyl functionality of ring A to a ketone functionality and the non-aromatic unsaturated ring B to a saturated ring.

25. A method of claim 24 wherein the reactant compound is

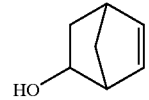

and the polycyclic compound containing a ketone functionality is,

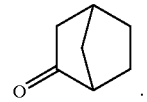

* * * * *